(12) United States Patent
Park et al.

(10) Patent No.: US 11,513,066 B2
(45) Date of Patent: Nov. 29, 2022

(54) APPARATUS AND METHOD FOR ESTIMATING BIO-INFORMATION

(71) Applicant: SAMSUNG ELECTRONICS CO., LTD., Suwon-si (KR)

(72) Inventors: Jin Young Park, Hwaseong-si (KR); Sung Mo Ahn, Yongin-si (KR); Kun Sun Eom, Yongin-si (KR); Hyeong Seok Jang, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 275 days.

(21) Appl. No.: 16/885,441

(22) Filed: May 28, 2020

(65) Prior Publication Data
US 2021/0172867 A1    Jun. 10, 2021

(30) Foreign Application Priority Data
Dec. 4, 2019   (KR) .................. 10-2019-0159809

(51) Int. Cl.
| | |
|---|---|
| *G01J 5/02* | (2022.01) |
| *G01N 21/31* | (2006.01) |
| *A61B 5/024* | (2006.01) |
| *A61B 5/00* | (2006.01) |
| *G01N 21/49* | (2006.01) |
| *G01N 21/59* | (2006.01) |

(52) U.S. Cl.
CPC ......... *G01N 21/314* (2013.01); *A61B 5/0075* (2013.01); *A61B 5/02427* (2013.01); *A61B 5/6898* (2013.01); *A61B 5/7225* (2013.01); *G01N 21/49* (2013.01); *G01N 2021/3181* (2013.01); *G01N 2021/5957* (2013.01)

(58) Field of Classification Search
CPC ................ G01N 21/314; G01N 21/49; G01N 2021/3181; G01N 2021/5957; G01N 21/474; G01N 2201/021; A61B 5/0075; A61B 5/02427; A61B 5/6898; A61B 5/7225; A61B 5/681; A61B 5/14535; A61B 5/14546; A61B 5/1455; A61B 5/7221; A61B 5/1172; A61B 5/7275; G06V 40/12
See application file for complete search history.

(56) References Cited

U.S. PATENT DOCUMENTS

| | | |
|---|---|---|
| 6,083,485 A | 7/2000 | Licha et al. |
| 6,205,354 B1 | 3/2001 | Gellermann et al. |
| 6,258,340 B1 | 7/2001 | Licha et al. |

(Continued)

FOREIGN PATENT DOCUMENTS

| | | |
|---|---|---|
| EP | 1 181 940 A2 | 2/2002 |
| JP | 3930334 B2 | 6/2007 |

(Continued)

*Primary Examiner* — Kiho Kim
(74) *Attorney, Agent, or Firm* — Sughrue Mion, PLLC

(57) ABSTRACT

An apparatus for estimating bio-information includes an optical sensor including a light source configured to emit light of multiple wavelengths onto an object, and including a plurality of detectors configured to detect light of each wavelength which is scattered or reflected from the object. The apparatus includes a processor configured to obtain spectra based on light of each wavelength which is detected by each detector, determine valid spectra of the obtained spectra, and estimate a bio-information value based on the valid spectra.

18 Claims, 13 Drawing Sheets

(56) References Cited

U.S. PATENT DOCUMENTS

| | | | |
|---|---|---|---|
| 6,913,743 B2 | 7/2005 | Licha et al. | |
| 6,926,885 B2 | 8/2005 | Licha et al. | |
| 6,993,372 B2* | 1/2006 | Fine | A61B 5/6826 600/335 |
| 7,025,949 B2 | 4/2006 | Licha et al. | |
| 7,445,767 B2 | 11/2008 | Licha et al. | |
| 7,655,217 B2 | 2/2010 | Licha et al. | |
| 8,260,402 B2 | 9/2012 | Ermakov et al. | |
| 9,464,986 B2 | 10/2016 | Chau et al. | |
| 9,526,431 B2 | 12/2016 | Zakharov et al. | |
| 9,788,730 B2 | 10/2017 | Noto et al. | |
| 9,814,417 B2 | 11/2017 | Sharifzadeh et al. | |
| 9,867,559 B2 | 1/2018 | Sato | |
| 9,888,855 B2 | 2/2018 | Kang et al. | |
| 10,349,847 B2 | 7/2019 | Kwon et al. | |
| 2005/0106106 A1 | 5/2005 | Licha et al. | |
| 2005/0169844 A1 | 8/2005 | Licha et al. | |
| 2005/0197581 A1 | 9/2005 | Ferguson et al. | |
| 2005/0197582 A1 | 9/2005 | Ferguson et al. | |
| 2005/0278184 A1 | 12/2005 | Fralick et al. | |
| 2010/0129293 A1 | 5/2010 | Licha et al. | |
| 2012/0330164 A1 | 12/2012 | Ermakov et al. | |
| 2014/0058224 A1 | 2/2014 | Gellermann et al. | |
| 2015/0223749 A1 | 8/2015 | Park et al. | |
| 2017/0251926 A1 | 9/2017 | Yoon et al. | |
| 2018/0132766 A1 | 5/2018 | Lee et al. | |
| 2018/0160908 A1 | 6/2018 | Kim et al. | |
| 2019/0076032 A1 | 3/2019 | Park et al. | |
| 2019/0200866 A1 | 7/2019 | Eom et al. | |
| 2019/0226975 A1* | 7/2019 | Osborne | G01N 15/1436 |

FOREIGN PATENT DOCUMENTS

| | | |
|---|---|---|
| JP | 2010-131243 A | 6/2010 |
| JP | 6218908 B2 | 10/2017 |
| KR | 10-0845640 B1 | 7/2008 |
| KR | 10-2011-0038020 A | 4/2011 |
| KR | 10-2017-0087381 A | 7/2017 |
| KR | 10-2002589 B1 | 7/2019 |
| KR | 10-2005312 B1 | 7/2019 |

* cited by examiner

APPARATUS AND METHOD FOR ESTIMATING BIO-INFORMATION

CROSS-REFERENCE TO RELATED APPLICATION(S)

This application is based on and claims priority under 35 U.S.C. § 119 to Korean Patent Application No. 10-2019-0159809, filed on Dec. 4, 2019, in the Korean Intellectual Property Office, the disclosure of which is incorporated by reference herein in its entirety.

BACKGROUND

1. Field

The disclosure relates to an apparatus and method for estimating bio-information, and more particularly to technology for non-invasively estimating antioxidant levels.

2. Description of Related Art

Reactive oxygen species act as an important biological defense factor such as white blood cells protecting the body against infections. However, it has been known that excessive generation of reactive oxygen species in the body may lead to various tissue diseases. Common factors that cause the reactive oxygen species include stress, alcohol, peroxides, medicine, and the like. The reactive oxygen species produced by these factors may cause cranial nerve diseases, circulatory diseases, cancer, digestive tract diseases, liver diseases, arteriosclerosis, renal diseases, diabetes, aging, and the like. Our bodies have a series of antioxidant defense systems to protect against oxygen toxicity. For normal operation of the systems, it is essential to consume a sufficient amount of antioxidants such as vitamin E vitamin C, carotenoid, flavonoid, and the like, and it is important to eat as many foods that are rich in antioxidants as possible for an effective antioxidant action. Accordingly, there is a need for an apparatus for easily identifying the amount of antioxidants in the body.

SUMMARY

Additional aspects will be set forth in part in the description which follows and, in part, will be apparent from the description, or may be learned by practice of the presented embodiments.

According to an aspect of an example embodiment, an apparatus for estimating bio-information includes an optical sensor including a light source configured to emit light of multiple wavelengths onto an object, and including a plurality of detectors configured to detect light of each wavelength which is scattered or reflected from the object. The apparatus includes a processor configured to obtain spectra based on light of each wavelength which is detected by each detector, determine valid spectra of the obtained spectra, and estimate a bio-information value based on the valid spectra.

The optical sensor includes a pixel array having a circular shape or a polygonal shape, the light source is disposed on a central pixel of the pixel array, and each of the plurality of detectors is disposed on a respective pixel around the central pixel.

The light source includes at least one of a light emitting diode (LED), a laser diode (LD), and a phosphor, and is formed of an array of a plurality of light sources to emit light of multiple wavelengths.

The processor is further configured to sequentially drive each wavelength of the light source with a time difference, and based on an intensity of light of each wavelength which is sequentially detected by each detector in response to the driving of the each wavelength with a time difference, obtain the spectra for each detector.

The processor is further configured to extract a light intensity for the each wavelength based on full width at half maximum (FWHM) properties of the light source which emits light of each wavelength.

The processor is further configured to determine the valid spectra based on at least one of high quality index (HQI) verification, hemoglobin index verification, and object contact position verification.

The processor is further configured to calculate, as an HQI, similarity between each spectrum and a reference spectrum, and determine spectra, having the calculated HQI which is greater than or equal to a predetermined threshold value, to be the valid spectra.

The processor is further configured to obtain hemoglobin signals at least at two wavelengths for each spectrum, calculate, as a hemoglobin index, at least either a ratio or a difference between the obtained hemoglobin signals, and determine the valid spectra by comparing the calculated hemoglobin index with a predetermined threshold value.

The processor is further configured to determine a contact position of the object based on fingerprint information generated when the object touches the optical sensor, and determine the valid spectrum based on the determined contact position.

The processor is further configured to in response to a plurality of objects being registered, identify an identifier of an object based on the fingerprint information, and based on the identified identifier of the object, perform at least one of user authentication, the determining of the contact position, and the determining of the valid spectra.

The processor is further configured to perform the HQI verification, and perform the hemoglobin index verification or the contact position verification on spectra having passed the HQI verification.

The processor is further configured to, based on obtaining the spectra for each of the plurality of detectors, construct a two dimensional (2D) map of the spectra, and determine the valid spectra based on the 2D map of the spectra.

The processor is further configured to generate a spectrum by combining the valid spectra for each wavelength, and obtain an estimated bio-information value based on the generated spectrum.

The processor is further configured to estimate a plurality of bio-information values based on each of the valid spectra, and obtain a final estimated bio-information value by combining the estimated plurality of bio-information values.

The bio-information value includes at least one of an antioxidant substance, blood glucose, triglyceride, cholesterol, calories, protein, carotenoid, lactate, and uric acid.

According to an aspect of an example embodiment, a method of estimating bio-information may include emitting light of multiple wavelengths onto an object by using a multi-wavelength light source, detecting light of each wavelength, which is scattered or reflected from the object, by using a plurality of detectors, obtaining spectra based on light of each wavelength which is detected by each detector, determining valid spectra of the obtained spectra, and estimating a bio-information value based on the valid spectra.

The emitting of the light of multiple wavelengths includes sequentially driving each wavelength of the multi-wavelength light source with a time difference. The obtaining of the spectra includes obtaining the spectra based on an intensity of light of each wavelength which is sequentially detected by each detector in response to the driving of the each wavelength with a time difference.

The obtaining of the spectra includes extracting a light intensity for the each wavelength based on full width at half maximum (FWHM) properties of the light source which emits light of each wavelength.

The determining the valid spectra includes determining the valid spectra based on at least one of high quality index (HQI) verification, hemoglobin index verification, and object contact position verification.

The estimating of the bio-information value comprises generating a spectrum by combining the valid spectra, and obtaining an estimated bio-information value based on the generated spectrum, or estimating a plurality of bio-information values based on each of the valid spectra, and obtaining a final estimated bio-information value by combining the estimated plurality of bio-information values.

BRIEF DESCRIPTION OF THE DRAWINGS

The above and other aspects, features, and advantages of certain embodiments of the present disclosure will be more apparent from the following description taken in conjunction with the accompanying drawings, in which.

Figure 1:
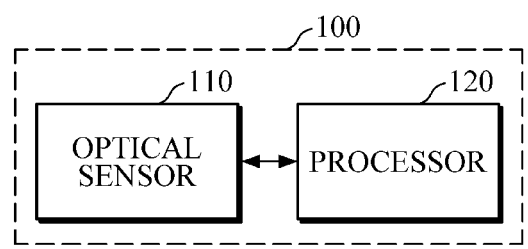
FIG. 1 is a block diagram illustrating an apparatus for estimating bio-information according to an embodiment.

Throughout the drawings and the detailed description, unless otherwise described, the same drawing reference numerals may refer to the same elements, features, and structures. The relative size and depiction of these elements, features, and structures may be exaggerated for clarity, illustration, and convenience.

DETAILED DESCRIPTION

Details of the embodiments are included in the following detailed description and drawings. Advantages and features of the present disclosure, and a method of achieving the same will be more clearly understood from the following embodiments described in detail with reference to the accompanying drawings. Throughout the drawings and the detailed description, unless otherwise described, the same drawing reference numerals may refer to the same elements, features, and structures.

It should be understood that, although terms such as "first," "second," etc. may be used herein to describe various elements, these elements should not be limited by these terms. These terms may be used to distinguish one element from another. Any references to the singular form of a term may include the plural form of the term unless expressly stated otherwise. In addition, unless explicitly described to the contrary, expressions such as "comprising" or "including" will be understood to imply the inclusion of stated elements but not the exclusion of any other elements. Also, terms such as "part," "module," etc., should be understood as a unit that performs at least one function or operation, and that may be embodied as hardware, software, or a combination thereof.

Hereinafter, embodiments of an apparatus and method for estimating bio-information will be described in detail with reference to the accompanying drawings. The embodiments of the apparatus for estimating bio-information may be mounted in a smartphone, a tablet personal computer (PC), a wearable device, a desktop computer, a laptop computer, as well as medical equipment in medical institutions, and the like.

Figure 2:
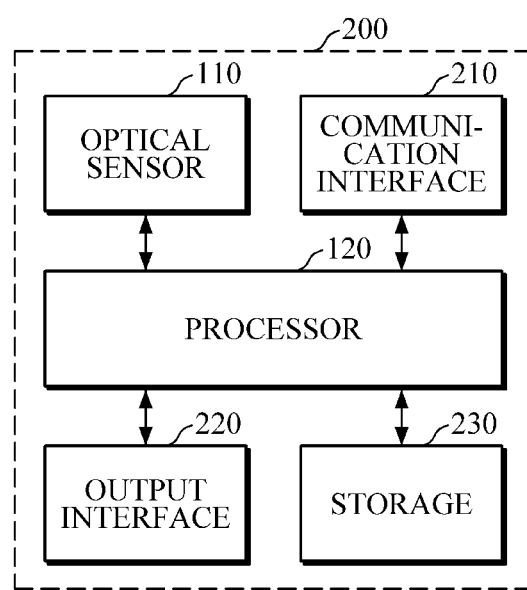
FIG. 2 is a block diagram illustrating an apparatus for estimating bio-information according to an embodiment.
Figure 3:
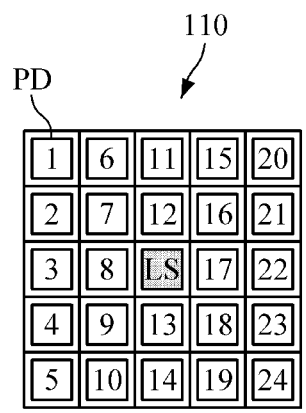
FIG. 3 is a diagram schematically illustrating an example of a structure of an optical sensor according to an embodiment.

FIG. 1 is a block diagram illustrating an apparatus for estimating bio-information according to an embodiment; FIG. 2 is a block diagram illustrating an apparatus for estimating bio-information according to an embodiment; FIG. 3 is a diagram schematically illustrating an example of a structure of an optical sensor according to an embodiment; and FIGS. 4A to 4E are diagrams explaining an example of verifying validity of a spectrum according to an embodiment.

Referring to FIGS. 1 and 2, the apparatuses 100 and 200 for estimating bio-information may include an optical sensor 110 and a processor 120.

The optical sensor 110 may emit light of multiple wavelengths onto an object when the object touches the optical sensor 110, and may detect light of multiple wavelengths which is scattered or reflected from the object. In this case, the object may be skin tissue of the human body such as, for example, the back of the hand, the wrist, fingers, and the like, at which veins or capillaries are located, or may be a body part at which the radial artery is located, but is not limited thereto.

The optical sensor 110 includes a multi-wavelength light source for emitting light of multiple wavelengths onto the object, and a detector for detecting light of multiple wavelengths which is scattered or reflected from the object. The light source may include a light emitting diode (LED), a laser diode (LD), a phosphor, and the like.

For example, in order to emit light of multiple wavelengths, the multi-wavelength light source may be formed of an array of a plurality of LEDs corresponding to each wavelength. However, the light source is not limited thereto, and may be formed of one LED which emits light of a single wavelength, and may be controlled to emit light of multiple wavelengths by using a temperature regulator, a filter, and the like, of the LED.

The detector may include a photo diode or a photo transistor (PTr). For example, the detector may be formed of an array of a plurality of photo diodes, each of which may detect light of multiple wavelengths emitted by the multi-wavelength light source.

Referring to FIG. 3, the optical sensor 110 according to an embodiment may be composed of a pixel array having a plurality of pixels. As illustrated in FIG. 3, the multi-wavelength light source LS is disposed on a central pixel, and the detectors PD are disposed on pixels around the central pixel. The multi-wavelength light source LS disposed on a central pixel may be an LED array having a plurality of small LEDs arranged in the form of an array, in which each LED may be preset to emit light of a corresponding wavelength.

While FIG. 3 illustrates an example of a pixel array including a multi-wavelength light source disposed on the central pixel, and 24 detectors arranged around the light source, the size of the pixel array is not limited thereto. While FIG. 3 illustrates a pixel array having a square shape, the shape of the pixel array is not limited thereto. For example, the multi-wavelength light source may be arranged at the center, and a plurality of detectors may be arranged around the light source in various polygonal shapes such as a circle, a square, a rectangle, a triangle, a pentagon, a hexagon, and the like.

The optical sensor 110 may be electrically connected to the processor 120. The multi-wavelength light source may sequentially drive each wavelength with a time difference under the control of the processor 120 to emit light of each wavelength to an object with a time difference. For example, the optical sensor 110 may emit light of each wavelength for a predetermined duration by sequentially controlling ON/OFF of each LED of an LED array, which emits light of multiple wavelengths, according to a predetermined driving sequence, e.g., starting from a short wavelength to a long wavelength.

When light of each wavelength, which is emitted sequentially with a time difference by the light source, is scattered or reflected from the object, the plurality of detectors arranged around the light source may sequentially detect the scattered or reflected light of each wavelength. The plurality of detectors may convert an optical signal of each wavelength, which is sequentially detected, into an electric signal, and may transmit the signal to the processor 120.

In this case, driving conditions of the optical sensor 110 may be preset. For example, the driving conditions may include information on a driving sequence, a duration, a light intensity, and the like, of each LED. Further, when the light source at each wavelength is driven, all the detectors, arranged around the light source, may be driven at the same time, or only some detectors positioned at different distances from the light source may be driven. In addition to the driving conditions of the light source, the driving conditions of the optical sensor 110 may further include driving conditions of the detectors, as described above.

The processor 120 may control driving of the optical sensor 110 based on the preset optical sensor driving conditions, and may construct a spectrum for each detector based on an intensity of light of each wavelength which is sequentially detected by each detector of the optical sensor 110. For example, once light of each wavelength is detected by each detector, the processor 120 may extract a light intensity for each wavelength based on full width at half maximum (FWHM) properties of an LED which emits light of each wavelength, and may construct spectra for the entire wavelength based on the extracted light intensity for each wavelength. However, the spectrum construction is not limited thereto.

Upon constructing the spectra for each detector, the processor 120 may construct a 2D map of the spectra. FIG. 4B illustrates an example of a 2D map of spectra for each of detectors PD1 to PD24 in a structure of the optical sensor 110 illustrated in FIG. 3, in which spectra for some detectors are omitted for convenience of explanation.

Upon constructing the spectra for each of the detectors, the processor 120 may verify validity of the spectra, and may estimate bio-information by using spectra having passed the validity verification. In this case, bio-information relates to antioxidant levels in the human body, and may include, for example, carotenoid. However, the bio-information is not limited thereto, and information, such as blood glucose, triglyceride, cholesterol, calories, protein, lactate, uric acid, and the like, may also be estimated.

For example, the processor 120 may verify the validity of each spectrum based on high quality index (HQI) verification, hemoglobin Index verification, object contact position verification, and the like. The processor 120 may perform only one of the verification methods, e.g., HQI verification. Alternatively, by sequentially applying two or more verification methods as needed, the processor 120 may determine only a spectrum most suitable for estimating antioxidant levels. For example, upon first performing the HQI verification, the processor 120 may perform the hemoglobin index verification or object contact position verification on spectra having passed the HQI verification.

For example, the processor 120 may calculate, as an HQI, similarity between each of a plurality of spectra, obtained for each detector, and a reference spectrum, and may perform the HQI verification for determining a spectrum, having the calculated HQI which is greater than a predetermined threshold value, to be a valid spectrum. In this case, the processor 120 may calculate the similarity by using various similarity calculation algorithms, such as Euclidean distance, Manhattan Distance, Cosine Distance, Mahalanobis Distance. Jaccard Coefficient, Extended Jaccard Coefficient. Pearson's Correlation Coefficient, Spearman's Correlation Coefficient, and the like.

Figure 4A:
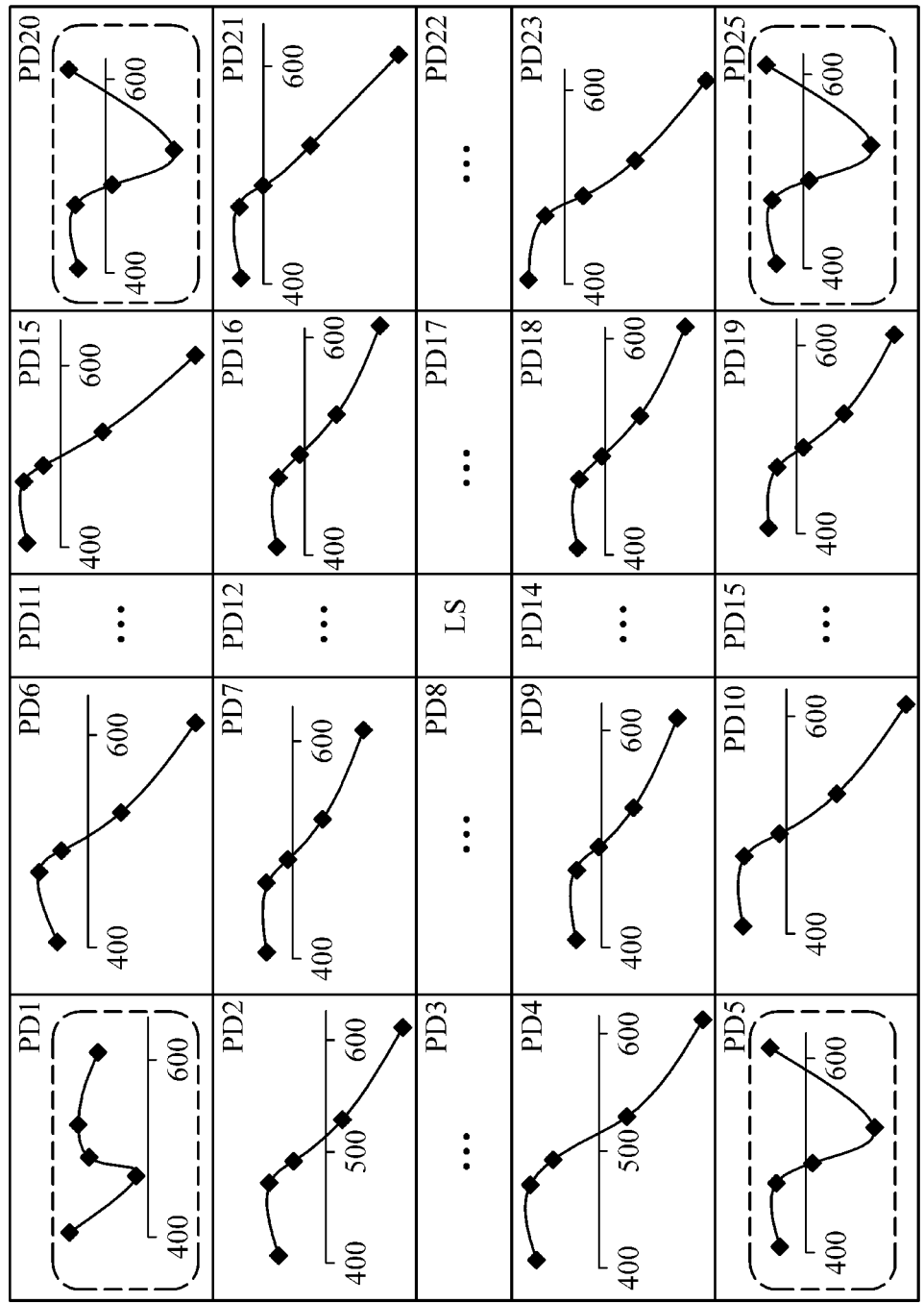
FIGS. 4A to 4E are diagrams explaining an example of verifying validity of a spectrum according to an embodiment.
Figure 4B:
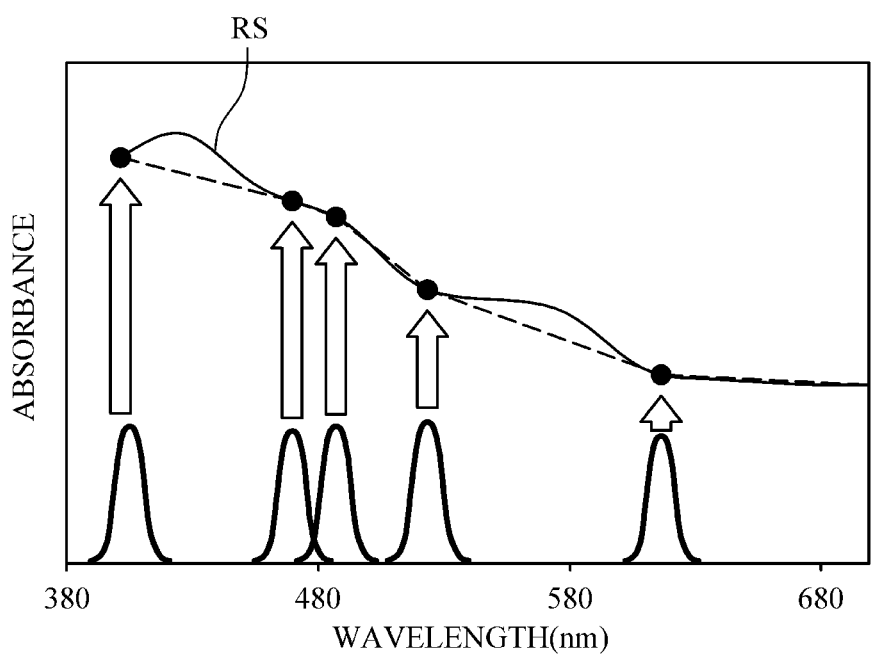

Referring to FIGS. 4A and 4B, it can be seen that some pixels PD1, PD5, PD20, and PD24 of spectra of FIG. 4A are not similar to a reference spectrum RS of FIG. 4B. As described above, the processor 120 may calculate, as an HQI, similarity between each of the spectra and the reference spectrum RS, and may determine the pixels PD1, PD5, PD20, and PD24, having HQI values which do not satisfy the predetermined threshold value, to be invalid spectra, and may determine the remaining spectra to be valid spectra. In this case, the reference spectrum may be a general spectrum obtained for a plurality of users by an external apparatus for obtaining a spectrum. Alternatively, the reference spectrum may be an individualized spectrum obtained by performing calibration using the apparatuses 100 and 200 for estimating bio-information while a user is at rest.

In another example, the processor 120 may calculate a hemoglobin index for each spectrum, and may perform the hemoglobin index verification for determining a spectrum, having the calculated hemoglobin index which is less than or equal to a predetermined threshold value, to be a valid spectrum. In this case, the predetermined threshold value may be preset by considering pressure at which an antioxidant signal is saturated and stabilized, i.e., a threshold pressure.

Figure 4C:
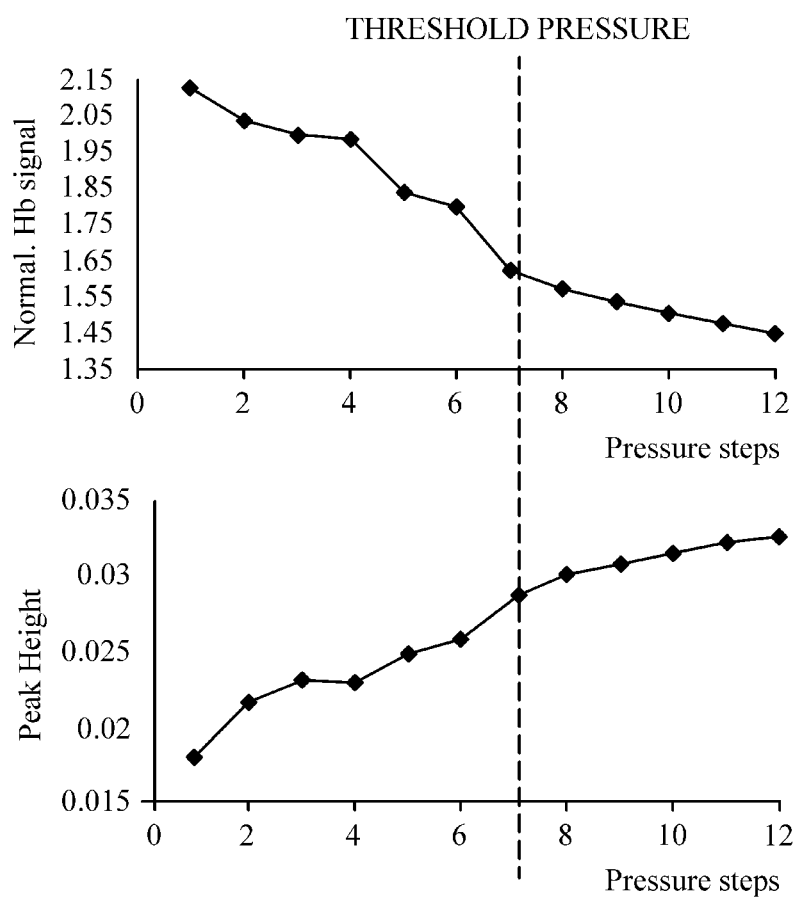

Referring to FIG. 4C, as can be seen from the lower view, a peak height of an antioxidant signal increases as pressure applied to the skin increases, and at a pressure greater than or equal to a predetermined threshold pressure, the antioxidant signal is saturated and stabilized. In this case, it can be seen that a coefficient of variation (CV) of the peak height of the antioxidant signal decreases as pressure applied to the skin increases. Further, as can be seen from the upper view of FIG. 4C, a hemoglobin signal (normal, Hb signal) in the skin decreases as pressure applied to the skin increases. Accordingly, it can be seen that a change trend of the hemoglobin signal according to a pressure change is similar to a change trend of the coefficient of variation of the antioxidant signal according to a pressure change.

The processor 120 may obtain hemoglobin signals at two wavelengths for each spectrum, and may calculate, as a hemoglobin index, at least either a ratio or a difference between the obtained hemoglobin signals.

Figure 4D:
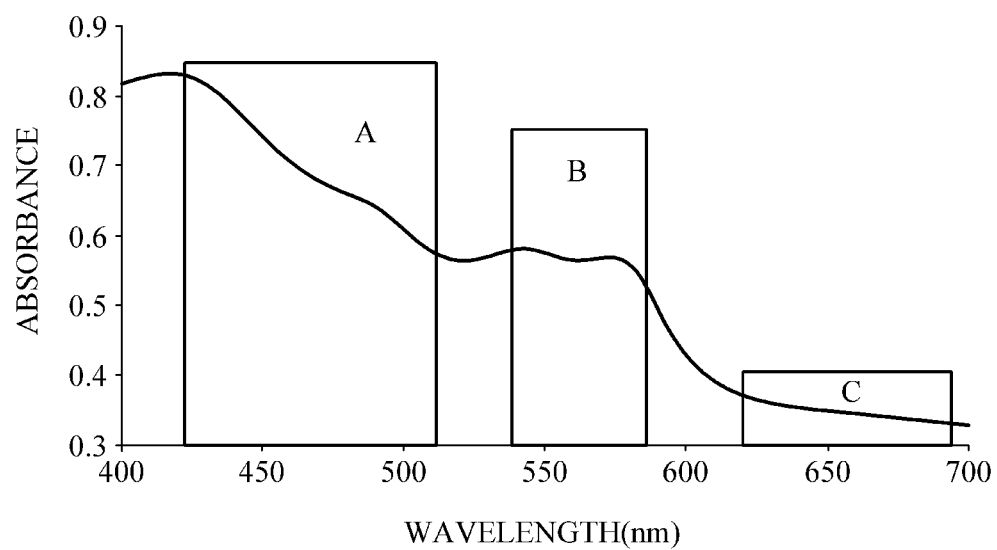

Referring to FIG. 4D, the processor 120 may obtain, as a hemoglobin index, a value obtained by normalizing a signal at a first wavelength by using a signal at a second wavelength for each spectrum, e.g., a ratio (B/C) between the signal at the first wavelength B and the signal at the second wavelength C. However, the hemoglobin index is not limited thereto, and the processor 120 may obtain a difference between the signals at the two wavelengths and the like as the hemoglobin index. In this case, the first wavelength may be a green wavelength B included in a wavelength band in which a hemoglobin signal is measured, i.e., an absorption band of hemoglobin, and the second wavelength may be a red wavelength C included in a wavelength band in which a base signal for normalizing the first wavelength is measured.

If the hemoglobin index of each spectrum is less than the predetermined threshold value, the processor 120 may determine the spectrum to be a spectrum which is valid for measuring an antioxidant signal. In addition, the processor 120 may estimate an antioxidant level based on an antioxidant signal at a blue wavelength A included in a third wavelength band of the valid spectrum, e.g., an absorption band of an antioxidant substance, as illustrated in FIG. 4D.

Figure 4E:
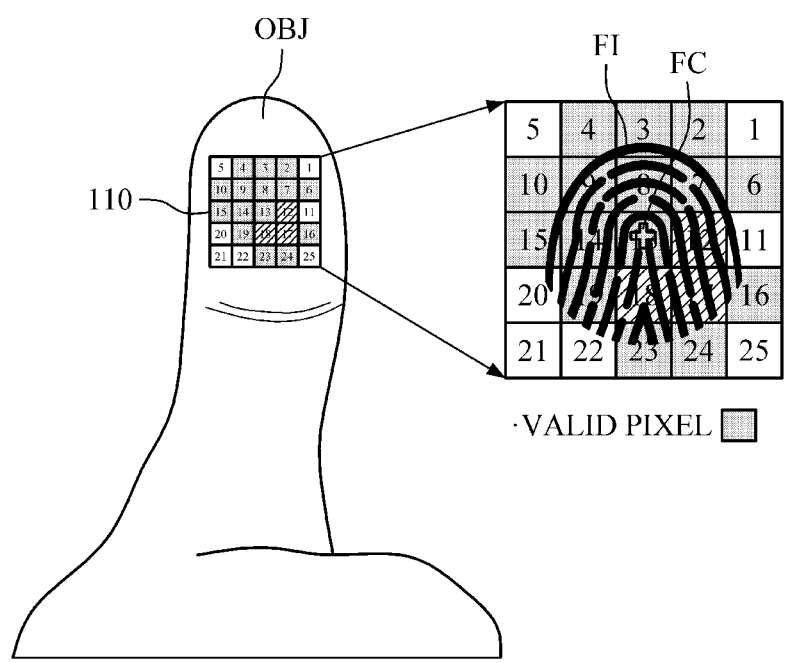

In yet another example, the processor 120 may obtain a contact position of an object which is in contact with the optical sensor 110, and may determine a valid spectrum based on the obtained contact position. Referring to FIG. 4E, the processor 120 may obtain a fingerprint FI when the object OBJ touches the optical sensor 110. To this end, the apparatuses 100 and 200 for estimating bio-information may further include a fingerprint sensor on a top portion or a bottom portion of the optical sensor 110. The fingerprint sensor may be an optical sensor, a capacitive sensor, or an ultrasonic sensor, but is not limited thereto.

Upon obtaining the fingerprint FI, the processor 120 may determine a region, such as a circle, a square, and the like, of a predetermined size as a fingerprint region by dividing a fingerprint outline or based on a fingerprint center (FC). However, this is merely an example, and the fingerprint region is not limited thereto.

For example, the processor 120 may determine, as a fingerprint region, a region of a predetermined size, e.g., a rectangular region having pixels 2, 4, 22, and 23 as vertices, along the fingerprint orientation based on the fingerprint center (FC). Upon determining the fingerprint region, the processor 120 may determine pixels 2, 3, 4, 7, 8, 9, 12, 13, 14, 17, 18, 19, 22, 23, and 24 in the fingerprint region as valid pixels, and may determine spectra of the valid pixels as valid spectra.

In addition, the apparatuses 100 and 200 for estimating bio-information may be mounted in a device which may be shared by a plurality of users, e.g., a large home appliance such as a refrigerator, a television (TV), and the like, or a device of a medical institution. In this case, each user may register an object to be used. Further, each user may set criteria for determining a valid spectrum, such as a method for verifying a valid spectrum and/or criteria for determining a contact position and the like, based on a type of the registered object (e.g., thumb, index finger, upper portion of the wrist, palm of the hand, etc.) and user characteristics (e.g., health condition, age, sex, temperature and humidity of an object, etc.).

Alternatively, the apparatuses 100 and 200 for estimating bio-information may be mounted in a device generally used only by a specific user, e.g., a wearable device, a smartphone, a tablet PC, and the like. The user may register, if necessary, a plurality of objects (e.g., thumb, index finger, upper portion of the wrist, etc.), and may properly set criteria for determining a valid spectrum for each object.

Upon obtaining the fingerprint FI from the object, the processor 120 may identify an ID of the object, which is in contact with the optical sensor 110, among the plurality of objects by using the obtained fingerprint FI. For example, upon identifying the ID of the object, the processor 120 may perform user authentication to determine whether to perform a function of estimating bio-information and/or to control use of other devices in which the apparatuses 100 and 200 for estimating bio-information are mounted. In another example, upon identifying the ID of the object, the processor 120 may check criteria for determining a valid spectrum corresponding to the identified ID of the object, and may determine a contact position and may verify a valid spectrum according to the criteria for determining a valid spectrum.

Furthermore, by applying together other verification methods described above, e.g., HQI verification and hemoglobin index verification, the processor 120 may classify some valid pixels as invalid pixels or may classify some invalid pixels as valid pixels. For example, referring to FIG. 4E, some pixels 12, 17, 18, and 22 in the fingerprint region are shown as invalid pixels. This shows a case in which the pixels 12, 17, and 18, which fail to pass hemoglobin index verification, are excluded from a group of valid pixels, and the pixel 22, which fails to pass HQI verification, is also excluded therefrom. Further, it can be seen that some pixels 6, 10, 15, and 16 in a region outside the fingerprint region are shown as valid pixels. This shows a case in which the pixels, which pass HQI verification and/or hemoglobin index verification, are classified as valid pixels. To this end, classification criteria according to verification methods, e.g., information on an order of priority of applying verification methods and the like, may be preset.

Upon determining valid spectra by performing validity verification, the processor 120 may estimate bio-information by using the valid spectra. When performing the hemoglobin index verification, the processor 120 may also estimate a bio-information value by using only a signal in an interval, in which an antioxidant signal is extracted by applying a pressure greater than or equal to a threshold pressure.

For example, the processor 120 may extract a feature for estimating an antioxidant value from the valid spectra, and may obtain an estimated antioxidant value by using an antioxidant value estimation model which defines a correlation between the feature and the antioxidant value. For example, the processor 120 may obtain antioxidant values for each of a plurality of valid spectra by using the antioxidant value estimation model, and may determine a statistical value (e.g., mean value, median value, mode, etc.) of all or some of the obtained antioxidant values to be a final antioxidant value. In another example, the processor 120 may obtain one spectrum by applying a pre-defined combination function to the plurality of valid spectra, and may obtain a final antioxidant value by using the obtained one spectrum and the antioxidant value estimation model.

Referring to FIG. 2, the apparatus 200 for estimating bio-information includes a communication interface 210, an output interface 220, and a storage 230.

The communication interface 210 may communicate with an external device by using wired or wireless communication techniques. For example, upon connection to an external device, the communication interface 210 may transmit and receive a variety of information related to estimating bio-information to and from the external device. For example, the communication interface 210 may transmit a bio-information estimation result to the external device, and may receive a variety of information related to estimating bio-information from the external device. In this case, the external device may include medical equipment in medical institutions, a personal information processing device, such as a smartphone, a tablet PC, a desktop computer, a laptop computer, and a wearable device, and the like.

The communication interface 210 may communicate with the external device by using communication techniques such as Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, third generation (3G), fourth generation (4G), and fifth generation (5G) telecommunications, and the like. However, this is merely exemplary and is not intended to be limiting.

The output interface 220 may output a processing result of the processor 120, and may provide the result for a user. The output interface 220 may output an estimated bio-information value such as an antioxidant value, and/or a warning or recommendation in response to the estimated bio-information value, and the like. For example, if the antioxidant value is less than or equal to a predetermined threshold value, the processor 120 may generate a recommendation to increase the antioxidant value. For example, if an antioxidant value is less than or equal to a predetermined threshold value, the processor 120 may generate a recommendation, such as "eat more vegetables," "cut down on smoking," "cut down on alcohol consumption," "exercise more," "reduce stress," and the like.

The output interface 220 may visually display the processing result by using a display module, or may display the result in a non-visual manner such as by voice, vibrations, tactile sensation, and the like, using a speaker module, a haptic module, and the like. Further, if an antioxidant value falls outside of a normal range, the output interface 220 may output warning information in various manners, such as highlighting an abnormal value in red, and the like, displaying the abnormal value along with a normal range, outputting a voice warning message, adjusting a vibration intensity, and the like.

The storage 230 may store a variety of information generated or collected by the optical sensor 110, the processor 120, and the communication interface 210. Further, the storage 230 may store reference information related to estimating bio-information. In this case, the reference information may include user characteristic information, such as a user's age, sex, health condition, and the like, a reference spectrum, a bio-information estimation model, and the like, but is not limited thereto.

In this case, the storage 230 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Figure 5:
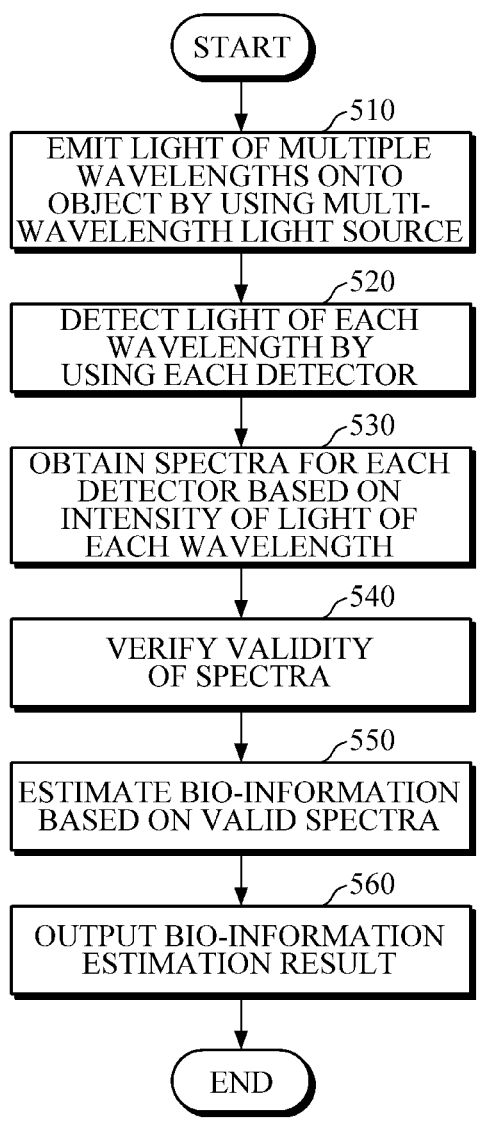
FIG. 5 is a flowchart illustrating a method of estimating bio-information according to an embodiment.
Figure 6:
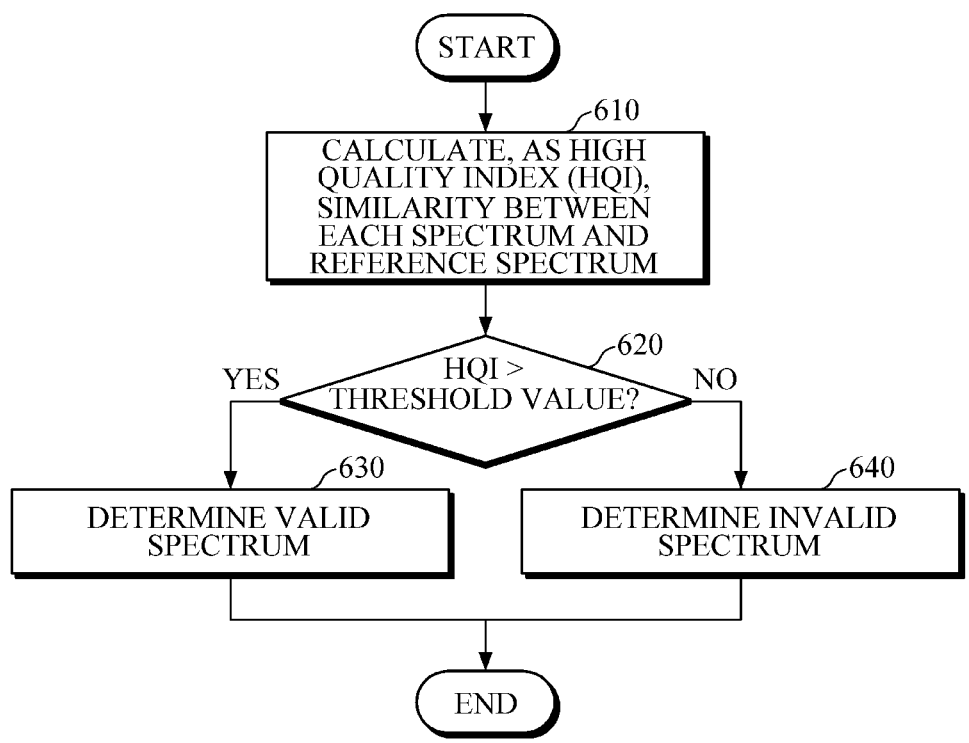
FIGS. 6 to 8 are diagrams illustrating examples of verifying validity according to an embodiment.
Figure 7:
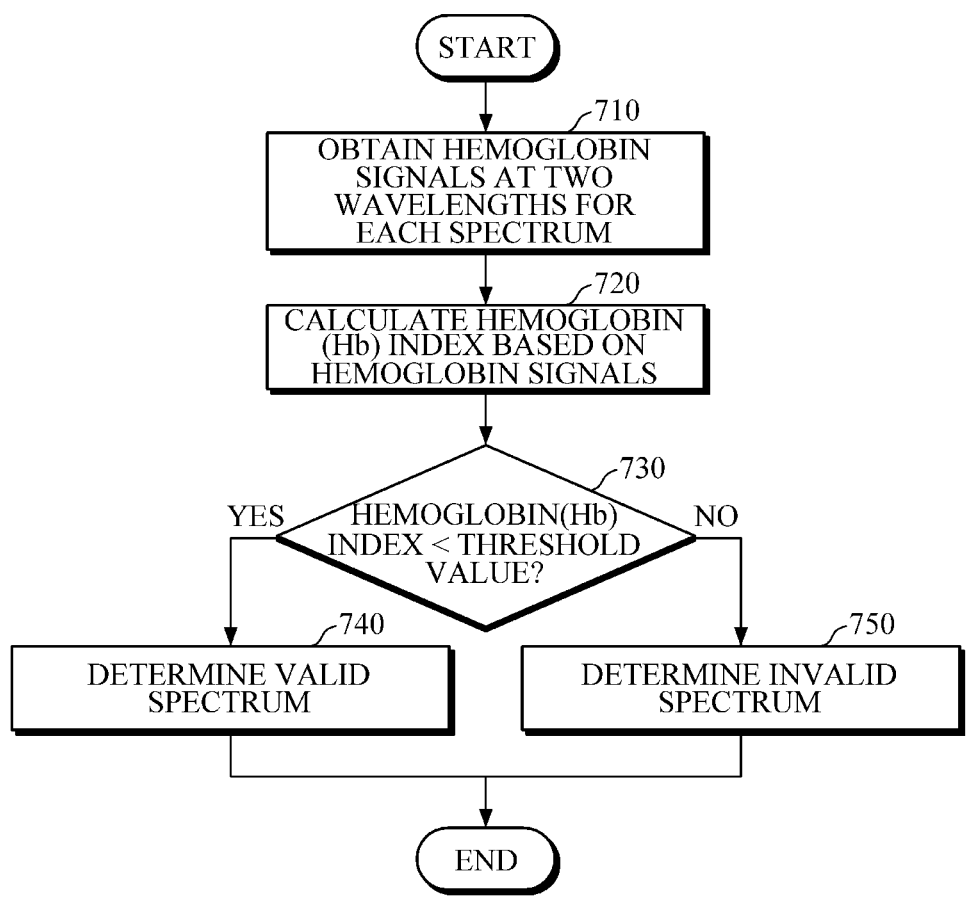
Figure 8:
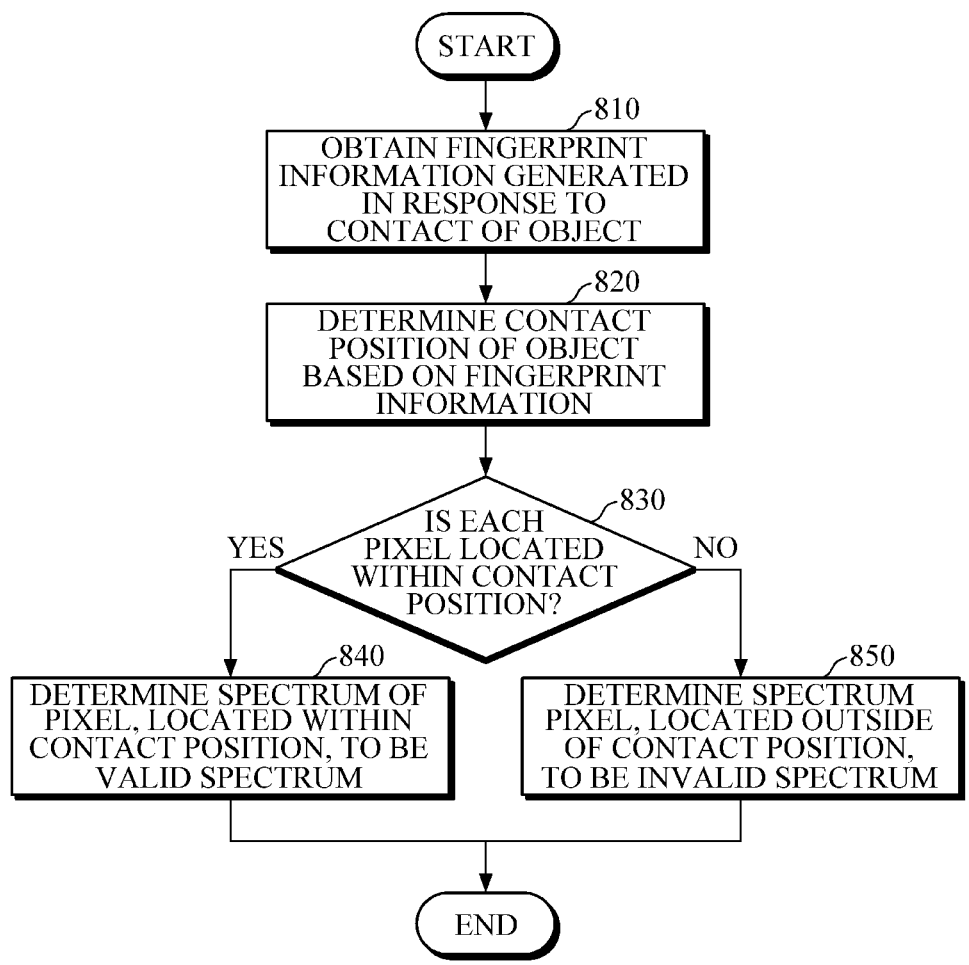

FIG. 5 is a flowchart illustrating a method of estimating bio-information according to an embodiment. FIGS. 6 to 8 are diagrams illustrating examples of verifying validity according to an embodiment. The methods of FIGS. 5 to 8 may be performed by the aforementioned embodiments of the apparatuses 100 and 200 for estimating bio-information, which are described above in detail and thus will be briefly described below.

In response to a request for estimating bio-information, the apparatuses 100 and 200 for estimating bio-information may drive a multi-wavelength light source to emit light of multiple wavelengths onto an object in operation 510. In this case, the multi-wavelength light source may be formed of an array of a plurality of light sources. Each light source may be driven with a time difference to sequentially emit light of each wavelength onto the object.

Then, by using a plurality of detectors which are arranged around the multi-wavelength light source, with some of the detectors being positioned at different distances from the multi-wavelength light source, the apparatuses 100 and 200 for estimating bio-information may sequentially detect light of each wavelength which is scattered or reflected from the object in operation 520.

Subsequently, the apparatuses 100 and 200 for estimating bio-information may obtain spectra for each detector based on an intensity of light of each wavelength which is detected by each detector in 530. For example, the apparatuses 100 and 200 for estimating bio-information may extract a light intensity for each wavelength based on full width at half maximum (FWHM) properties of an LED which emits light of each wavelength, and may construct spectra based on the extracted light intensity for each wavelength.

Next, the apparatuses 100 and 200 for estimating bio-information may verify validity of the obtained spectra in operation 540.

For example, as illustrated in FIGS. 6 to 8, the apparatuses 100 and 200 for estimating bio-information may perform HQI verification, hemoglobin index verification, object contact position verification, and the like. Based on the computing performance, types of bio-information to be estimated, and various other criteria, the apparatuses 100 and 200 for estimating bio-information may perform any one or two or more of the verification methods of FIGS. 6 to 8. In this case, spectra, having passed any one verification, may be secondarily verified by using another verification method.

Referring to FIG. 6, upon obtaining the spectra in operation 530, the apparatuses 100 and 200 for estimating bio-information may calculate, as an HQI, similarity between each of the spectra and a preset reference spectrum in operation 610. Then, the apparatuses 100 and 200 for estimating bio-information may compare the HQI with a predetermined threshold value in operation 620, may determine a spectrum, having the HQI which is greater than the predetermined threshold value, to be a valid spectrum in operation 630, and may determine a spectrum, having the HQI which is lower than the predetermined threshold value, to be an invalid spectrum in operation 640.

Referring to FIG. 7, upon obtaining the spectra in operation 530, the apparatuses 100 and 200 for estimating bio-information may obtain hemoglobin signals at two wavelengths for each spectrum in operation 710. For example, the apparatuses 100 and 200 for estimating bio-information may obtain a signal at a first wavelength, e.g., a green wavelength, which is included in an absorption band of hemoglobin, and may obtain a signal at a second wavelength, e.g., a red wavelength, at which a base signal for normalizing the signal at the first wavelength may be measured.

Then, the apparatuses 100 and 200 for estimating bio-information may calculate, as a hemoglobin index, a value obtained by dividing the signal at the first wavelength by the signal at the second wavelength, or by subtracting the signal at the second wavelength from the signal at the first wavelength in operation 720.

Subsequently, the apparatuses 100 and 200 for estimating bio-information may compare the calculated hemoglobin index with a predetermined threshold value in operation 730, may determine a spectrum, having a hemoglobin index which is less than the predetermined threshold value, to be a valid spectrum in operation 740, and may determine a spectrum, having a hemoglobin index which is greater than the predetermined threshold value, to be an invalid spectrum in operation 750.

Referring to FIG. 8, the apparatuses 100 and 200 for estimating bio-information may obtain fingerprint information, e.g., a fingerprint image, which is generated when an object touches an optical sensor in operation 810. Then, the apparatuses 100 and 200 for estimating bio-information may determine a contact position of the object based on the fingerprint information in operation 820. For example, the apparatuses 100 and 200 for estimating bio-information may obtain a fingerprint region by dividing a fingerprint outline in the fingerprint image, and may determine the obtained fingerprint region to be the contact position of the object. Alternatively, the apparatuses 100 and 200 for estimating bio-information may obtain a fingerprint center in the fingerprint image, and may determine a region of a predetermined size based on the fingerprint center to be the contact position of the object. However, the contact position is not limited thereto.

Then, the apparatuses 100 and 200 for estimating bio-information may determine whether each pixel of the optical sensor is located within the contact position of the object in operation 830, may determine a spectrum of a pixel, located within the contact position, to be a valid spectrum in operation 840, and may determine a spectrum of a pixel, located outside of the contact position, to be an invalid spectrum in operation 850.

Referring back to FIG. 5, the apparatuses 100 and 200 for estimating bio-information may estimate bio-information in operation 550 based on the valid spectra having passed the validity verification in operation 540. In this case, the apparatuses 100 and 200 for estimating bio-information may estimate bio-information by using a bio-information estimation model which defines a correlation between the spectrum and the bio-information. For example, the apparatuses 100 and 200 for estimating bio-information may estimate bio-information for each of a plurality of valid spectra, and may obtain a statistical value of estimated bio-information values to be a final estimated bio-information value. Alternatively, the apparatuses 100 and 200 for estimating bio-information may obtain one spectrum by combining the plurality of valid spectra, and may obtain a final estimated bio-information value by using the obtained one spectrum.

Then, the apparatuses 100 and 200 for estimating bio-information may output a bio-information estimation result in operation 560. In this case, the apparatuses 100 and 200 for estimating bio-information may provide a user with information, such as the estimated bio-information values, warnings, recommendation, and the like, by various visual/non-visual methods using a display, a speaker, and a haptic device.

Figure 9:
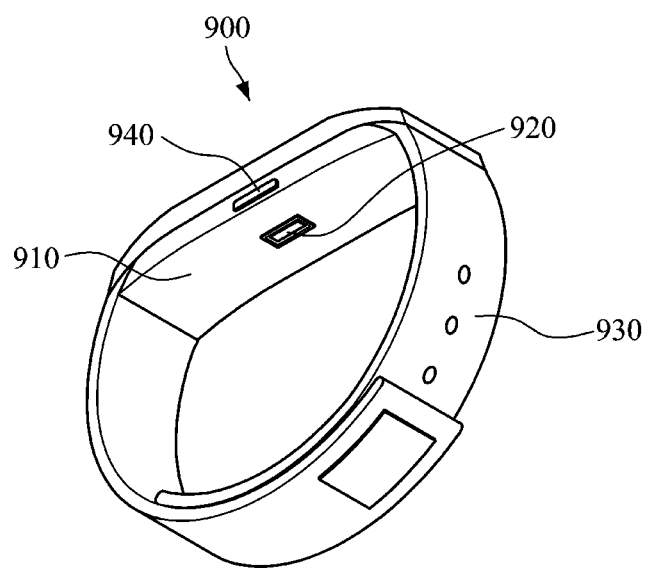
FIG. 9 is a diagram illustrating an example of a wearable device according to an embodiment.

FIG. 9 is a diagram illustrating an example of a wearable device, to which embodiments of an apparatus for estimating bio-information are applied.

The apparatuses 100 and 200 for estimating bio-information according to the embodiments described above may be mounted in the wearable device 900. While FIG. 9 illustrates a smart watch-type wearable device 900, the wearable device is not limited thereto, and may be modified to various information processing devices such as a smartphone, a tablet PC, and the like.

Referring to FIG. 9, the wearable device 900 includes a main body 910 and a strap 930 and various modules of the aforementioned apparatuses 100 and 200 for estimating bio-information may be mounted in the main body 910.

The strap 930 may be made of a flexible material and may be connected to the main body 910. The strap 930 may be bent to be wrapped around a user's wrist or may be bent in a manner which allows the strap 930 to be detached from the wrist. In this case, a battery may be embedded in the main body 910 or the strap 930 to supply power to the wearable device 900.

As illustrated in FIG. 9, an optical sensor 920 may be mounted on a rear surface of the main body 910 at a position which comes into contact with a user's wrist. As illustrated in FIG. 3, the optical sensor 920 may be composed of a pixel array having a square shape or a circular shape, in which a multi-wavelength light source may be disposed at the center of the optical sensor 920 and a plurality of detectors may be disposed around the light source.

A processor, a storage, and a communication interface may be mounted in the main body 910 of the wearable device 900.

The processor may construct spectra for each detector by using light detected by each detector. Further, the processor may determine valid spectra by verifying validity of the constructed spectra, and may obtain, for example, an estimated antioxidant value by using the determined valid spectra.

A display of an output interface may be mounted on a front surface of the main body 910, and may output a variety of information for a user. Further, the display may include a touch screen for receiving a user's touch input, and may receive the touch input and transmit the touch input to the processor. In addition, the main body 910 of the wearable device 900 may include a manipulator 940 for operating a function of estimating bio-information and various other functions of the wearable device 900 (e.g., a clock function, a music function, a video data function, a text messaging function, etc.). The manipulator 940 may receive a user's command, and may transmit the command to the processor. Further, the manipulator 940 may include a power button to turn on/off the wearable device 900.

The embodiments of the present disclosure can be implemented by computer-readable code written on a non-transitory computer-readable medium. The non-transitory computer-readable medium may be any type of recording device in which data is stored in a computer-readable manner.

Examples of the non-transitory computer-readable medium include a ROM, a RAM, a CD-ROM, a magnetic tape, a floppy disc, an optical data storage, and a carrier wave (e.g., data transmission through the Internet). The non-transitory computer-readable medium can be distributed over a plurality of computer systems connected to a network so that computer-readable code is written thereto and executed therefrom in a decentralized manner. Functional programs, codes, and code segments for implementing the embodiments of the present disclosure can be deduced by computer programmers of ordinary skill in the art, to which the present disclosure pertains.

The present disclosure has been described herein with regard to various embodiments. However, it will be obvious to those skilled in the art that various changes and modifications can be made without changing technical ideas and departing from the scope of the present disclosure. Thus, it is clear that the above-described embodiments are illustrative in all aspects and are not intended to limit the present disclosure.

What is claimed is:

1. An apparatus for estimating bio-information, the apparatus comprising:
   an optical sensor including a light source configured to emit light of multiple wavelengths onto an object, and including a plurality of detectors configured to detect light of each wavelength which is scattered or reflected from the object; and
   a processor configured to:
   extract a light intensity of each wavelength based on full width at half maximum (FWHM) properties of the light source;
   obtain spectra based on the light intensity of each wavelength which is detected by each of the plurality of detectors;
   determine valid spectra of the obtained spectra; and
   estimate a bio-information value based on the valid spectra.

2. The apparatus of claim 1, wherein the optical sensor includes a pixel array having a circular shape or a polygonal shape,
   wherein the light source is disposed on a central pixel of the pixel array, and
   wherein each of the plurality of detectors is disposed on a respective pixel around the central pixel.

3. The apparatus of claim 1, wherein the light source includes at least one of a light emitting diode (LED), a laser diode (LD), and a phosphor, and is formed of an array of a plurality of light sources to emit the light of multiple wavelengths.

4. The apparatus of claim 1, wherein the processor is further configured to:
   sequentially drive each wavelength of the light source with a time difference; and
   based on an intensity of light of each wavelength which is sequentially detected by each of the plurality of detectors in response to the driving of the each wavelength with the time difference, obtain the spectra for each of the plurality of detectors.

5. The apparatus of claim 1, wherein the processor is further configured to:
   determine the valid spectra based on at least one of high quality index (HQI) verification, hemoglobin index verification, and object contact position verification.

6. The apparatus of claim 5, wherein the processor is further configured to:
   calculate, as an HQI, similarity between each spectrum and a reference spectrum; and
   determine the spectra, having the calculated HQI which is greater than or equal to a predetermined threshold value, to be the valid spectra.

7. The apparatus of claim 5, wherein the processor is further configured to:
   obtain hemoglobin signals at least at two wavelengths for each of the spectra;
   calculate, as a hemoglobin index, at least either a ratio or a difference between the obtained hemoglobin signals; and
   determine the valid spectra by comparing the calculated hemoglobin index with a predetermined threshold value.

8. The apparatus of claim 5, wherein the processor is further configured to:
   determine a contact position of the object based on fingerprint information generated when the object touches the optical sensor; and
   determine the valid spectrum based on the determined contact position.

9. The apparatus of claim 8, wherein the processor is further configured to:
   in response to a plurality of objects being registered, identify an identifier of the object based on the fingerprint information; and
   based on the identified identifier of the object, perform at least one of user authentication, the determining of the contact position, and the determining of the valid spectra.

10. The apparatus of claim 5, wherein the processor is further configured to:
    perform the HQI verification; and
    perform the hemoglobin index verification or the contact position verification on the spectra having passed the HQI verification.

11. The apparatus of claim 5, wherein the processor is further configured to:
    based on obtaining the spectra for each of the plurality of detectors, construct a two dimensional (2D) map of the spectra; and
    determine the valid spectra based on the 2D map of the spectra.

12. The apparatus of claim 1, wherein the processor is further configured to:
    generate a spectrum by combining the valid spectra for each wavelength; and
    obtain an estimated bio-information value based on the generated spectrum.

13. The apparatus of claim 1, wherein the processor is further configured to:
    estimate a plurality of bio-information values based on each of the valid spectra; and
    obtain a final estimated bio-information value by combining the estimated plurality of bio-information values.

14. The apparatus of claim 13, wherein the bio-information value includes at least one of an antioxidant substance, blood glucose, triglyceride, cholesterol, calories, protein, carotenoid, lactate, and uric acid.

15. A method of estimating bio-information, the method comprising:
    emitting light of multiple wavelengths onto an object by using a multi-wavelength light source;
    detecting light of each wavelength, which is scattered or reflected from the object, by using a plurality of detectors;
    extracting a light intensity of each wavelength based on full width at half maximum (FWHM) properties of the multi-wavelength light source;
    obtaining spectra based on the light intensity of each wavelength which is detected by each of the plurality of detectors;
    determining valid spectra of the obtained spectra; and
    estimating a bio-information value based on the valid spectra.

16. The method of claim 15, wherein:
    the emitting of the light of multiple wavelengths comprises sequentially driving each wavelength of the multi-wavelength light source with a time difference; and the obtaining of the spectra comprises obtaining the spectra based on an intensity of light of each wavelength which is sequentially detected by each of the plurality of detectors in response to the driving of the each wavelength with the time difference.

17. The method of claim 15, wherein the determining the valid spectra comprises determining the valid spectra based on at least one of high quality index (HQI) verification, hemoglobin index verification, and object contact position verification.

18. The method of claim 17, wherein the estimating of the bio-information value comprises generating a spectrum by combining the valid spectra, and obtaining an estimated bio-information value based on the generated spectrum, or estimating a plurality of bio-information values based on each of the valid spectra, and obtaining a final estimated bio-information value by combining the estimated plurality of bio-information values.

* * * * *